(12) United States Patent
Cullen et al.

(10) Patent No.: US 8,461,410 B2
(45) Date of Patent: Jun. 11, 2013

(54) WOUND DRESSING MATERIALS COMPRISING COMPLEXES OF ANIONIC POLYSACCHARIDES WITH SILVER

(75) Inventors: Breda M. Cullen, Skipton (GB);
Deborah Addison, Keasden (GB);
David Greenhalgh, Skipton (GB);
Alicia Essler, Skipton (GB);
Sarah-Jayne Gregory, Guiseley (GB)

(73) Assignee: Ethicon, Inc., Somerville, NJ (US)

( * ) Notice: Subject to any disclaimer, the term of this patent is extended or adjusted under 35 U.S.C. 154(b) by 1091 days.

(21) Appl. No.: 10/527,421

(22) PCT Filed: Sep. 10, 2003

(86) PCT No.: PCT/GB03/03898
§ 371 (c)(1),
(2), (4) Date: Nov. 18, 2005

(87) PCT Pub. No.: WO2004/024197
PCT Pub. Date: Mar. 25, 2004

(65) Prior Publication Data
US 2006/0149182 A1  Jul. 6, 2006

Related U.S. Application Data

(60) Provisional application No. 60/414,381, filed on Sep. 30, 2002.

(30) Foreign Application Priority Data

Sep. 11, 2002 (GB) .................................. 0221062.3

(51) Int. Cl.
*A61F 13/00* (2006.01)

(52) U.S. Cl.
USPC .................................. 602/48; 602/41; 602/42

(58) Field of Classification Search
USPC .................. 602/46, 48, 41–42; 604/304–308
See application file for complete search history.

(56) References Cited

U.S. PATENT DOCUMENTS

| | | | | |
|---|---|---|---|---|
| 3,092,552 A | * | 6/1963 | Romans | 424/404 |
| 5,271,943 A | * | 12/1993 | Bogart et al. | 424/484 |
| 5,429,591 A | * | 7/1995 | Yamamoto et al. | 602/54 |
| 5,554,598 A | * | 9/1996 | Burger et al. | 514/54 |

(Continued)

FOREIGN PATENT DOCUMENTS

| | | |
|---|---|---|
| CA | 2430001 | 6/2002 |
| EP | 0541391 | 6/1998 |

(Continued)

OTHER PUBLICATIONS

Y.-S. Cho et al., "Hyaluronic acid and silver sulfadiazine-impregnated polyurethane foams for would dressing application", Journal of Materials Science: Materials in Medicine 13 (2002) 861-865.

(Continued)

*Primary Examiner* — Kim M Lewis
(74) *Attorney, Agent, or Firm* — Theodore J. Shatynski (57) ABSTRACT

The invention provides a wound dressing material comprising a complex of an anionic polysaccharide with silver, wherein the material comprises from about 0.1 wt. % to about 3 wt. % of silver. Also provided are wound dressings comprising such materials, and the use of such materials in medicine.

18 Claims, 6 Drawing Sheets

U.S. PATENT DOCUMENTS

| | | | |
|---|---|---|---|
| 5,744,151 A * | 4/1998 | Capelli | 424/405 |
| 6,409,881 B1 * | 6/2002 | Jaschinski | 162/9 |
| 6,565,878 B2 * | 5/2003 | Schoenfeldt et al. | 424/443 |
| 6,605,751 B1 * | 8/2003 | Gibbins et al. | 602/41 |
| 6,998,509 B1 * | 2/2006 | Nielsen | 602/48 |
| 2002/0177828 A1 * | 11/2002 | Batich et al. | 604/367 |
| 2002/0187181 A1 * | 12/2002 | Godbey et al. | 424/443 |
| 2007/0100269 A1 * | 5/2007 | Addison et al. | 602/48 |

FOREIGN PATENT DOCUMENTS

| | | |
|---|---|---|
| EP | 0437095 | 8/1999 |
| EP | 1153622 B1 | 10/2004 |
| GB | 748283 A | 4/1956 |
| GB | 1280631 | 7/1972 |
| GB | 2314840 A | 1/1998 |
| GB | 2314842 A * | 1/1998 |
| WO | WO 87/05517 A1 | 9/1987 |
| WO | WO 90/10020 A1 | 9/1990 |
| WO | WO 91/11206 A1 | 8/1991 |
| WO | WO 96/13282 A1 | 5/1996 |
| WO | WO 96/35720 A1 | 11/1996 |
| WO | WO 98/00180 A | 1/1998 |
| WO | WO 98/00446 | 1/1998 |
| WO | WO 00/09173 A1 | 2/2000 |
| WO | WO 00/33893 | 6/2000 |
| WO | WO 01/24839 A1 | 4/2001 |
| WO | WO 01/24841 A1 | 4/2001 |
| WO | WO 02/24240 A1 | 3/2002 |
| WO | WO 02/36866 A1 | 5/2002 |
| WO | WO 02/43743 | 6/2002 |

OTHER PUBLICATIONS

Y.S. Cho et al., "Studies on gelatin-based sponges. Part III: A comparative study of cross-linked gelatin/alginate, gelatin/hyaluronate and chitosan/hyaluronate sponges and their application as a wound dressing in full-thickness skin defect of rat", Journal oif Materials Science: Materials in Medicine 12 (2001) 67-73.

International Search Report re: PCT/GB03/03898 dated Dec. 30, 2003.

Hidalgo, E. et al. 'Silver Nitrate: Antimicrobial Activity Related to Cytotoxicity in Cultured Human Fibroblasts' Skin Pharmacol Appl Skin Physiol (1998) vol. 11 pp. 14-151 (1998).

Hidalgo, E., et al 'Study of cytotoxicity mechanisms of silver nitrate in human dermal fibroblasts' Toxicology Letters (1998) vol. 98 pp. 169-179.

Hollinger, M.A., 'Toxicological Aspects of Topical Silver Pharmaceuticals' Critical Reviews in Toxicology (1996) 26(2) pp. 255-260.

Innes, M.E. et al., 'The use of silver coated dressings on donor site wounds: a prospective, controlled matched pair study.' Burns (2001) vol. 27 pp. 621-627.

* cited by examiner

WOUND DRESSING MATERIALS COMPRISING COMPLEXES OF ANIONIC POLYSACCHARIDES WITH SILVER

CROSS-REFERENCE TO RELATED APPLICATIONS

This application is a National Stage application under 35 U.S.C. §371 of PCT/GB03/03898 filed Sep. 10, 2003, which claims priority from GB0221062.3, filed Sep. 11, 2002 and U.S. Provisional Application Ser. No. 60/414,381 filed Sep. 30, 2002.

BACKGROUND OF THE INVENTION

1. Field of the Invention

The present invention relates to wound dressing materials comprising complexes formed between anionic polysaccharides, such as oxidized regenerated cellulose (ORC), and silver, and to the uses thereof for the treatment of wounds.

2. Background of the Invention

Anionic polysaccharides such as alginates, hyaluronic acid and its salts, and oxidized celluloses such as oxidized regenerated cellulose (ORC) are known for use as wound dressing materials. Alginates and ORC are hemostatic when applied to a wound.

EP-A-0437095 describes the preparation of a neutralized ORC fabric by reacting ORC with a buffered solution of a salt of a weak acid, such as sodium acetate. The use of a buffered reagent is said to result in less breakdown of ORC fabrics. The neutralized ORC can support further acid-sensitive hemostatic agents such as thrombin or t-PA.

WO98/00180 describes the use of freeze-dried sponges of collagen admixed with oxidized regenerated cellulose (ORC) for the treatment of chronic wounds. The mixed sponges provide enhanced healing of chronic wounds such as venous ulcers, decubitis ulcers and diabetic ulcers. The specification mentions that silver sulfadiazine or chlorhexidine may be present as an antiseptic additive.

GB-A-748283 describes complexes of polysaccharides with various metals, including silver. WO91/11206 describes the use of silver alginate salts in wound dressings. WO87/05517 describes silver salts of hyaluronic acid that may be used as or in antimicrobial wound dressings.

WO02/43743 describes wound dressings comprising a silver salt of an anionic polysaccharide, and further comprising a substance to improve the photostability of the silver salt. The stabilising substance may include ammonia, ammonium salts, thiosulphates, chlorides and/or peroxides. In one preferred embodiment, the stabilising agent is aqueous ammonium chloride.

BRIEF SUMMARY OF THE INVENTION

The present invention provides a wound dressing material comprising a complex of an anionic polysaccharide with silver, wherein the material comprises from about 0.1 wt. % to about 3 wt. % of silver.

DETAILED DESCRIPTION OF THE INVENTION

The term "complex" refers to an intimate mixture at the molecular scale, preferably with ionic or covalent bonding between the silver and the polysaccharide. The complex preferably comprises a salt formed between the anionic polysaccharide and $Ag^+$, but it may also comprise silver clusters and/or colloidal silver metal, for example produced by exposure of the complex to light.

Preferably, the anionic polysaccharide is a polycarboxylate. Suitable anionic polysaccharides include alginates, hyaluronates, pectins, carrageenans, xanthan gums, sulfated dextrans, cellulose derivatives such as carboxymethyl celluloses, and oxidized celluloses.

The term "oxidized cellulose" refers to any material produced by the oxidation of cellulose, for example with dinitrogen tetroxide. Such oxidation converts primary alcohol groups on the saccharide residues to carboxylic acid groups, forming uronic acid residues within the cellulose chain. The oxidation generally does not proceed with complete selectivity, and as a result hydroxyl groups on carbons 2 and 3 are occasionally converted to the keto form. These keto units introduce an alkali-labile link, which at pH 7 or higher initiates the decomposition of the polymer via formation of a lactone and sugar ring cleavage. As a result, oxidized cellulose is biodegradable and bioabsorbable under phsyiological conditions.

The preferred oxidized cellulose for use in the present invention is oxidized regenerated cellulose (ORC) prepared by oxidation of a regenerated cellulose, such as rayon. It has been known for some time that ORC has haemostatic properties. ORC has been available as a haemostatic fabric called SURGICEL (Registered Trade Mark of Johnson & Johnson Medical, Inc.) since 1950. This product is produced by the oxidation of a knitted rayon material.

Preferably, the anionic polysaccharide is substantially insoluble in water at pH7. Preferably, the anionic polysaccharide has a molecular weight greater than about 20,000, more preferably greater than about 50,000. Preferably, the anionic polysaccharide is in the form of a film, or fibers having length greater than 1 mm.

Preferably the amount of silver in the complex is from about 0.1% to about 50% by weight based on the weight of the anionic polysaccharide, more preferably from about 1% to about 40%, still more preferably from about 2% to about 30% by weight, and most preferably from about 5% to about 25%.

It has been found that the silver-containing complexes are suitable for use in the preparation of antimicrobial wound dressing materials. The silver confers antimicrobial properties on the wound dressing. More surprisingly, at low concentrations of about 0.1 wt. % to about 3 wt. %, the silver in the complex exhibits a proliferative effect on wound healing cells and therefore is expected to promote wound healing even when the complexes according to the invention are applied directly to a wound. The oligodynamic effect of silver on cells in culture is known—this is usually regarded as affecting the growth of both bacteria and cells. It is therefore surprising to find that silver in the dressings of the present invention can have the opposite effect on certain cells of importance to wound healing.

It has also been found, surprisingly, that wound dressing materials containing the above-defined low levels of silver exhibit a surprising ability to inhibit the production of TNF-α and IL-1. This is expected to result in beneficial anti-inflammatory properties of the wound dressing materials.

The wound dressing materials according to the present invention may be in any convenient form, such as a powder, microspheres, flakes, a mat or a film.

In certain embodiments, the wound dressing material according to the present invention is in the form of a semisolid or gel ointment for topical application.

In certain embodiments, the wound dressing material according to the present invention is in the form of a freeze-dried or solvent-dried bioabsorbable sponge for application to a chronic wound. Preferably, the average pore size of the sponge is in the region of 10-500 μm, more preferably about 100-300 μm.

In yet other embodiments, the wound dressing material according to the present invention is in the form of a flexible film, which may be continuous or interrupted (e.g. perforated). The flexible film preferably comprises a plasticiser to render it flexible, such as glycerol.

Preferably, the wound dressing material is in the form of a sheet, for example a sheet of substantially uniform thickness. The area of the sheet is typically from about 1 cm$^2$ to about 400 cm$^2$, and the thickness typically from about 1 mm to about 10 mm. The sheet may for example be a freeze-dried sponge, or a knitted, woven or nonwoven fibrous sheet or a gel sheet. Preferably, the sheet comprises less than about 15% by weight of water.

Preferably, the wound dressing material comprises from about 0.1 wt % to 100 wt % of the silver-containing complex, more preferably from about 0.1 wt % to about 5 wt. %, for example from about 0.2 wt. % to about 2 wt. %.

The amount of silver in the wound dressing is from about 0.1 wt. % to about 0.3 wt. %. Lesser amounts of silver could give insufficient antimicrobial effect. Greater amounts of silver could give rise to antiproliferative effects on wound healing cells.

The wound dressing materials according to the present invention may further comprise one or more polysaccharides that have not been complexed to silver. These polysaccharides may include any one or more of the anionic polysaccharides listed above as being suitable for complexation with silver. The additional polysaccharides may additionally or alternatively comprise any other medically acceptable polysaccharides, such as for example cellulose, regenerated celluloses such as rayon, non-anionic cellulose derivatives such as hydroxyethyl cellulose, and starch derivatives.

The wound dressing materials according to the present invention may further comprise anionic polysaccharides that have been complexed to therapeutically effective metal ions other than silver, for example bismuth, copper, nickel, zinc, manganese, magnesium, gold, or mixtures thereof. Preferably, the amounts of such polysaccharides complexed to other metals is from 0.001 to 10 wt. % of the dressing, more preferably from 0.01 to 1 wt % of the dressing. Preferably, the amounts of said other metals is from 10 to 10000 ppm, more preferably from about 50 to about 1000 ppm in the dressing.

The wound dressing materials according to the present invention may further comprise other medically acceptable materials besides polysaccharides, including textile fibers such as nylon or polyester staple fibers, nontextile fibers such as meltblown nylon fibers, and bioresorbable fibers such as polylactide/polyglycolide fibers. The other fibers may provide reinforcement and dilution of the polysaccharide. The other fibers are preferably present in an amount up to about 90 wt %, more preferably from about 25% to about 75 wt % of the wound dressing materials.

The wound dressing materials according to the present invention preferably further comprise collagen, in addition to the silver complex of an anionic polysaccharide. Preferably the amount of collagen in the dressing is from about 10% to about 90% by weight based on the dry weight of the wound dressing materials, more preferably from about 25% to about 75%.

The collagen may be selected from native collagens such as Types I, II or III native collagens, atelopeptide collagen, regenerated collagen and gelatin.

In certain embodiments, at least a portion of the collagen in the wound dressing materials is also complexed with silver. This can be achieved by treating the collagen with a solution of a silver salt. The silver salt may for example be silver acetate or silver nitrate at a concentration of about 0.01 molar to about 1 molar. The treatment is preferably carried out at a pH of from about 5 to about 9. It is thought that the silver complexes primarily to the nitrogen-containing side chains of the collagen amino acids, in particular to lysine, hydroxylysine, asparagine, glutamine and arginine. The silver could also bind to the sulfhydryl groups of methionine and cysteine residues, where present, and to carboxyl groups of aspartate and glutamate.

Preferably the amount of silver in the collagen complex is from about 0.01 to about 30% by weight based on the weight of the collagen, more preferably from about 0.1% to about 20%, more preferably from about 2% to about 10% by weight. Preferably, the amount of silver-collagen complex in the wound dressing material is from about 0.1 to about 10 wt. %, more preferably from about 0.1 to about 2 wt. %. In any case, the total amount of silver in the wound dressing material is generally as specified above.

In certain embodiments the dressing according to the present invention is fully resorbable. Preferably, the wound dressing materials according to the present invention are suitable for application directly to a wound surface.

Preferred wound dressing materials according to the present invention are silver-containing versions of the dressings according to WO98/00180 or EP-A-1153622, the entire contents of which are incorporated herein by reference. Briefly, these dressings are freeze-dried sponges that comprise a mixture of collagen and ORC, and that preferably consist essentially of such a mixture. Preferably, the weight ratio of collagen to ORC is about 40:60 to about 60:40. In the sponges according to the present invention, a portion of the ORC is replaced by a silver/ORC complex, and/or a portion of the collagen may be replaced by a silver/collagen complex. Preferably, from about 0.1 to about 50 wt. % of the ORC may be replaced by the silver-ORC complex, and a similar fraction of the collagen may similarly be replaced. It will be appreciated that silver ion exchange can take place between the collagen and the ORC in such collagen/ORC wound dressing materials.

Especially suitable wound dressing materials are freeze-dried sponges comprising from about 35 wt % to about 60 wt % of ORC, from about 60 wt. % to about 35 wt. % of a collagen, and from about 0.5% to about 5 wt. % of an ORC/silver complex, wherein the complex comprises from about 10 wt. % to about 40 wt. % of silver based on the dry weight of the complex. In preferred embodiments, the materials comprise from about 0.5 wt. % to about 2 wt. % of the ORC/silver complex. In preferred embodiments, the materials consist essentially of the collagen, ORC, and ORC/silver complex.

In another aspect, the present invention provides a wound dressing comprising a wound dressing material according to the invention. The wound dressing may consist of, or consist essentially of the wound dressing material according to the invention.

The wound dressing is preferably in sheet form and comprises an active layer of the wound dressing material according to the invention. The active layer would normally be the wound contacting layer in use, but in some embodiments it could be separated from the wound by a liquid-permeable top sheet. Preferably, the area of the active layer is from about 1 cm$^2$ to about 400 cm$^2$, more preferably from about 4 cm$^2$ to about 100 cm$^2$.

Preferably, the article further comprises a backing sheet extending over the active layer opposite to the wound facing side of the active layer. Preferably, the backing sheet is larger than the active layer such that a marginal region of width 1 mm to 50 mm, preferably 5 mm to 20 mm extends around the active layer to form a so-called island dressing. In such cases, the backing sheet is preferably coated with a pressure sensitive medical grade adhesive in at least its marginal region.

Preferably, the backing sheet is substantially liquid-impermeable. The backing sheet is preferably semipermeable. That is to say, the backing sheet is preferably permeable to water vapour, but not permeable to liquid water or wound exudate. Preferably, the backing sheet is also microorganism-impermeable. Suitable continuous conformable backing sheets will preferably have a moisture vapor transmission rate (MVTR) of the backing sheet alone of 300 to 5000 g/m$^2$/24 hrs, preferably 500 to 2000 g/m$^2$/24 hrs at 37.5° C. at 100% to 10% relative humidity difference. The backing sheet thickness is preferably in the range of 10 to 1000 micrometers, more preferably 100 to 500 micrometers.

The MVTR of the dressing according to the present invention as a whole is lower than that of the backing sheet alone, because the apertured sheet partially obstructs moisture transfer through the dressing. Preferably, the MVTR of the dressing (measured across the island portion of the dressing) is from 20% to 80% of the MVTR of the backing sheet alone, more preferably from 20% to 60% thereof, and most preferably about 40% thereof. It has been found that such moisture vapor transmission rates allow the wound under the dressing to heal under moist conditions without causing the skin surrounding the wound to macerate.

Suitable polymers for forming the backing sheet include polyurethanes and poly alkoxyalkyl acrylates and methacrylates such as those disclosed in GB-A-1280631. Preferably, the backing sheet comprises a continuous layer of a high density blocked polyurethane foam that is predominantly closed-cell. A suitable backing sheet material is the polyurethane film available under the Registered Trade Mark ESTANE 5714F.

The adhesive (where present) layer should be moisture vapor transmitting and/or patterned to allow passage of water vapor therethrough. The adhesive layer is preferably a continuous moisture vapor transmitting, pressure-sensitive adhesive layer of the type conventionally used for island-type wound dressings, for example, a pressure sensitive adhesive based on acrylate ester copolymers, polyvinyl ethyl ether and polyurethane as described for example in GB-A-1280631. The basis weight of the adhesive layer is preferably 20 to 250 g/m$^2$, and more preferably 50 to 150 g/m$^2$. Polyurethane-based pressure sensitive adhesives are preferred.

Further layers of a multilayer absorbent article may be built up between the active layer and the protective sheet. For example, these layers may comprise an apertured plastic film to provide support for the active layer in use, in which case the apertures in the film are preferably aligned in register with the apertures in the hydrogel layer.

The dressing may further comprise an absorbent layer between the active layer and the protective sheet, especially if the dressing is for use on exuding wounds. The optional absorbent layer may be any of the layers conventionally used for absorbing wound fluids, serum or blood in the wound healing art, including gauzes, nonwoven fabrics, superabsorbents, hydrogels and mixtures thereof. Preferably, the absorbent layer comprises a layer of absorbent foam, such as an open celled hydrophilic polyurethane foam prepared in accordance with EP-A-0541391, the entire content of which is expressly incorporated herein by reference. In other embodiments, the absorbent layer may be a nonwoven fibrous web, for example a carded web of viscose staple fibers. The basis weight of the absorbent layer may be in the range of 50-500 g/m$^2$, such as 100-400 g/m$^2$. The uncompressed thickness of the absorbent layer may be in the range of from 0.5 mm to 10 mm, such as 1 mm to 4 mm. The free (uncompressed) liquid absorbency measured for physiological saline may be in the range of 5 to 30 g/g at 25°. Preferably, the absorbent layer or layers are substantially coextensive with the chitosan/ORC layer.

The wound facing surface of the dressing is preferably protected by a removable cover sheet. The cover sheet is normally formed from flexible thermoplastic material. Suitable materials include polyesters and polyolefins. Preferably, the adhesive-facing surface of the cover sheet is a release surface. That is to say, a surface that is only weakly adherent to the active layer and the adhesive on the backing sheet to assist peeling of the hydrogel layer from the cover sheet. For example, the cover sheet may be formed from a non-adherent plastic such as a fluoropolymer, or it may be provided with a release coating such as a silicone or fluoropolymer release coating.

Preferably, the wound dressing materials and/or the wound dressings according to the present invention are sterile. Preferably, they are packaged in a microorganism-impermeable container. Preferably, the sterility assurance level is better than 10$^{-6}$. Preferably, the dressing has been sterilized by gamma-irradiation.

In a further aspect, the present invention provides the use of a complex of an anionic polysaccharide with silver for the preparation of a wound dressing material according to the present invention for the treatment of wounds, especially chronic wounds such as venous ulcers, decubitis ulcers or diabetic ulcers. Preferably, the treatment comprises applying the wound dressing material directly to the surface of the wound.

In a further aspect, the present invention provides a method of treatment of a wound, comprising applying to the wound a wound dressing material comprising an effective amount of a complex of an anionic polysaccharide and silver, whereby said complex is antimicrobially effective without exhibiting substantial antiproliferative activity against wound healing cells. Preferably, the wound dressing material is also effective to reduce inflammation. The method is especially suitable for treatment of chronic wounds such as venous ulcers, decubitis ulcers or diabetic ulcers.

It has also been found that the materials according to the present invention are surprisingly effective to inhibit the release of TNF-α from macrophages. This property is expected to render the materials effective in the treatment of inflammation. Accordingly, in a further aspect, the present invention provides the use of a complex of an anionic polysaccharide with silver for the preparation of a material comprising from about 0.1 wt. % to about 3 wt. % of silver for use in the treatment of inflammation.

The complex of an anionic polysaccharide and silver contained in the materials of the present invention can be made by a method comprising the step of treating an anionic polysaccharide with a solution of a silver salt. Preferably, the solution is an aqueous solution.

Preferably, the anionic polysaccharide is substantially insoluble in water at pH7, and the treatment is therefore carried out on the polysaccharide in the solid state. For example, the polysaccharide may be in the form of solid fibers, sheet, sponge or fabric. In certain embodiments, the anionic polysaccharide is a salt and the treatment therefore can be regarded as an ion exchange. In other embodiments, the anionic polysaccharide is at least partly in free acid form, in which case the silver salt is preferably a salt of a weak acid, for example silver acetate, whereby the anionic polysaccharide is at least partially neutralised by the silver salt. Similar processes are described in EP-A-0437095, the entire content of which is expressly incorporated herein by reference.

The neutralization reaction can be carried out in water or alcohol alone but is preferably carried out in mixtures of water and alcohols. The use of a mixture of water and alcohol provides good solubility for the weak acid salts via the water, and the alcohol prevents the anionic polysaccharide from excessively swelling, distorting and weakening during the neutralization. Thus the physical properties of the material are retained. Methanol is the preferred alcohol because many of the above-mentioned salts have good solubility in this alcohol in combination with water. Preferably, the alcohol to water ratio has a range of about 4:1 to 1:4. If the solution becomes too rich in alcohol, some salts may no longer be soluble particularly if the alcohol is other than methanol. If the solution becomes too rich in water, some swelling of the polysaccharide will occur as neutralization takes place and there will be some loss in physical properties such as in the tensile strength of the polysaccharide. Other useful alcohols include, for example, ethyl alcohol, propyl alcohol and isopropyl alcohol.

The use of a mild neutralizing agent such as silver acetate allows for control of the degree of neutralization. Use of stoichiometric and chemically equivalent amounts of neutralizing agent and carboxylic acid on the anionic polysaccharide does not produce a 100% neutralized polysaccharide as would be produced with strong irreversible reactions with bases such as sodium hydroxide, sodium carbonate, sodium bicarbonate and ammonium hydroxide.

Anionic polysaccharides behave as an ion exchanger and will pull out of solution the silver cation of any silver salt that is passed over them. The by-product of this exchange is an acid from the salt and by using a salt of a weak organic acid, a weak acid such as acetic acid is produced which does no damage to the polysaccharide. Using salts of strong acids such as sodium chloride or sodium sulfate produces hydrochloric acid or sulfuric acid by-products respectively, and these strong acids can cause damage such as depolymerization of the polysaccharide When using silver salts of weak acids, the silver ion is exchanged for a proton on the polysaccharide and part of the salt is converted to weak acid. The mixture of acid and salt in the solution results in a buffered solution which maintains a fairly constant pH and controls the degree of neutralization. An equilibrium reaction is established whereby the silver ions are bound to the acid portion of the polysaccharide and also to the salt molecules. This partitioning of the silver ions prevents the neutralization of the polysaccharide from going to completion.

Using a stoichiometric amount of, for example, silver acetate brings about a 65-75% degree of neutralization of the carboxylic acid groups on an oxidized cellulose polymer. This control of pH by creating a self generating buffered solution and the use of methanol to control the swelling of the material, leads to a partially neutralized material in which the physical properties, e.g. tensile strength and shape of the polysaccharide, are preserved.

The amount of silver salt used is generally about equal to or up to twice the stoichiometric amount of carboxylic acid content of the polysaccharide. Alternatively, a second charge of a stoichiometric amount of silver salt can be used if the reaction is recharged with fresh solvent and salt after the first charge reaches a constant pH. The material with elevated pH is then washed to remove the excess silver salt and ions therefrom.

It will be appreciated that the complexes obtainable by the methods described above may be used in the products and methods according to any aspect of the invention. More generally, any feature or combination of features that is described as preferred in connection with any one aspect of the invention or in connection with the above-described methods is also preferred in connection with every other aspect of the invention. Furthermore, any combination of the specific or preferred features disclosed herein is also encompassed within the scope of the disclosure.

EXAMPLES

Example 1

A complex of ORC with silver was prepared as follows.

A SURGICEL cloth (Johnson & Johnson Medical, Arlington) was milled using a rotary knife cutter through a screenplate, maintaining the temperature below 60° C., to provide a fibrous ORC powder Silver acetate powder (4.08 g) was dissolved in 800 mls of de-ionised water. After all the powder had dissolved to form a colourless, clear solution, the ORC milled fibers (5 g) were added to this solution. The ORC was then allowed to react for sixty minutes, or less if desired. The solution was then filtered and the fibers were collected and washed with either de-ionised water or alcohol. The silver complex of ORC was then allowed to dry at 37° C. overnight or until the fibers were dry. To reduce the darkening of the final product the solution and reacted fibers were protected from the light throughout the reaction.

Examples 2-7

Freeze-dried collagen/ORC sponges suitable for use as wound dressing materials according to the invention were prepared as follows.

First, the collagen component was prepared from bovine corium as follows. Bovine corium was split from cow hide, scraped and soaked in sodium hypochlorite solution (0.03% w/v) to inhibit microbial activity pending further processing.

The corium was then washed with water and treated with a solution containing sodium hydroxide (0.2% w/v) and hydrogen peroxide (0.02% w/v) to swell and sterilize the corium at ambient temperature.

The corium splits then underwent an alkali treatment step in a solution containing sodium hydroxide, calcium hydroxide and sodium bicarbonate (0.4% w/v, 0.6% w/v and 0.05% w.v, respectively) at pH greater than 12.2, ambient temperature, and for a time of 10-14 days, with tumbling, until an amide nitrogen level less than 0.24 mmol/g was reached.

The corium splits then underwent an acid treatment step with 1% hydrochloric acid at ambient temperature and pH 0.8-1.2. The treatment was continued with tumbling until the corium splits had absorbed sufficient acid to reach a pH less than 2.5. The splits were then washed with water until the pH value of corium splits reached 3.0-3.4.

The corium splits were then comminuted with ice in a bowl chopper first with a coarse comminution and then with a fine comminution setting. The resulting paste, which was made up in a ratio of 650 g of the corium splits to 100 g of water, as ice, was frozen and stored before use in the next stage of the process. However, the collagen was not freeze-dried before admixture with the ORC in the next stage.

The silver-ORC complex, unmodified milled ORC powder, and the required weight (according to solids content) of frozen collagen paste were then added to a sufficient amount of water acidified with acetic acid to obtain a pH value of 3.0 and a total solids content of 1.0%-2.0%, in the following proportions by weight:
Example 2: 45% Silver-ORC/55% Collagen
Example 3: 20% Silver-ORC+15% ORC/55% Collagen
Example 4: 10% Silver-ORC+35% ORC/55% Collagen
Example 5: 2% Silver-ORC+43% ORC/55% Collagen
Example 6: 1% Silver-ORC+44% ORC/55% Collagen
Example 7: 0.2% Silver-ORC+44.8% ORC/55% Collagen The mixture was homogenized through a Fryma MZ130D homogenizer, progressively diminishing the settings to form a homogeneous slurry. The pH of the slurry was maintained at 2.9-3.1. The slurry temperature was maintained below 20° C., and the solids content was maintained at 1%±0.07.

The resulting slurry was pumped to a degassing vessel. Vacuum was initiated for a minimum of 30 minutes, with intermittent stirring, to degas the slurry. The slurry was then pumped into freeze-drier trays to a depth of 25 mm. The trays were placed onto freezer shelves where the temperature has been preset to −40° C. The freeze-drier programme was then initiated to dry and dehydrothermally cross-link the collagen and ORC to form thick sponge pads.

On completion of the cycle, the vacuum was released, the freeze-dried blocks were removed, and were then split to remove the top and bottom surface layers, and to divide the remainder of the blocks into 3 mm-thick pads. The step of splitting the freeze-dried blocks into pads was carried out with a Fecken Kirfel K1 slitter.

Finally, the pads were die-cut to the desired size and shape on a die-cutter, packaged, and sterilized with 18-29 KGy of cobalt 60 gamma-irradiation. Surprisingly, this irradiation does not cause significant denaturation of the collagen, which appears to be stabilized by the presence of ORC. The resulting freeze-dried collagen ORC pads had a uniform, white, velvety appearance.

Examples 8-11

Collagen/ORC sponges were prepared from unmodified ORC and from collagen, wherein a fraction of the collagen had been replaced by a collagen-silver complex, as follows.

Silver acetate powder (1.48 g) was dissolved in 400 mls de-ionised water with stirring and warming.

Collagen slurry (417 g, containing 5 g solids at the percentage solids in the slurry of 1.2%) was added to the silver acetate solution and allowed to react for ten minutes stirring gently (If the collagen was allowed to react for longer it become stringy and was difficult to re-slurry in acetic acid).

The solution was filtered using the funnel and filter paper and the solids rinsed with de-ionised water. Squeezed out excess liquid in the solid by gently pressing between two filter papers. The collagen solids were protected from the light during this step and all following steps.

The solids were made up to a weight of 417 g using 0.05 M acetic acid. The mixture was placed into an Industrial Waring Blender and blended until a smooth slurry was achieved again.

Freeze dried sponges were then made as described above for Examples 2-7, with unmodified ORC and with replacement of a fraction of the collagen by the silver-complexed collagen slurry. These examples were considered to fall within the scope of the present invention because the silver in the silver-collagen comples will also complex and exchange with the ORC under the preparation conditions.

The following formulations were made:
Example 8: 55% Silver-Collagen/45% ORC
Example 9: 45% Silver-Collagen+10% Collagen/45% ORC
Example 10: 30% Silver-Collagen+25% Collagen/45% ORC
Example 11: 15% Silver-Collagen+40% Collagen/45% ORC
Procedure 1

The bactericidal activity of the sponges prepared in Examples 2 to 7 was tested on *pseudomonas Aeruginosa* and *staphylococcus Aureus* by looking at zone of inhibition.

Six 2 cm×2 cm squares of each sample were cut out in sterile conditions. On day one of the experiment cultures of both *Pseudomonas aeruginosa* and *Staphylococcus aureus* were incubated aerobically at 37° C. for 24 hours on Diagnostic Sensitivity Agar (DSA). After 24 hours test samples were each placed on a DSA plate and were immediately wetted with 0.5 mls of a buffer solution. Three squares of sample were placed on plates inoculated with *Pseudomonas aeruginosa* and three were placed on plates inoculated with *Staphylococcus aureus*. The plates were then incubated at 37° C. for 24 hours. The zone of inhibited growth around the sample was then measured using callipers and the test sample was placed on a new inoculated DSA plate. A swab test was carried out on the area beneath the sample to determine if the sample was bacteriostatic if not bactericidal by smearing the swab on a DSA plate and incubating it for 24 hours and then examining the growth. The samples were transferred onto fresh inoculated plates with the above procedure being carried out every 24 hours for 72 hours as long as the samples remain intact.

As a negative control, a freeze dried sponge of 45% ORC/55% collagen without any silver was tested. A commercially available silver-containing antimicrobial dressing (ACTICOAT, registered trade mark of Smith & Nephew) and silver nitrate solution (0.5%) were used as positive controls and zones of inhibition were observed for both over the test period.

Figure 1:
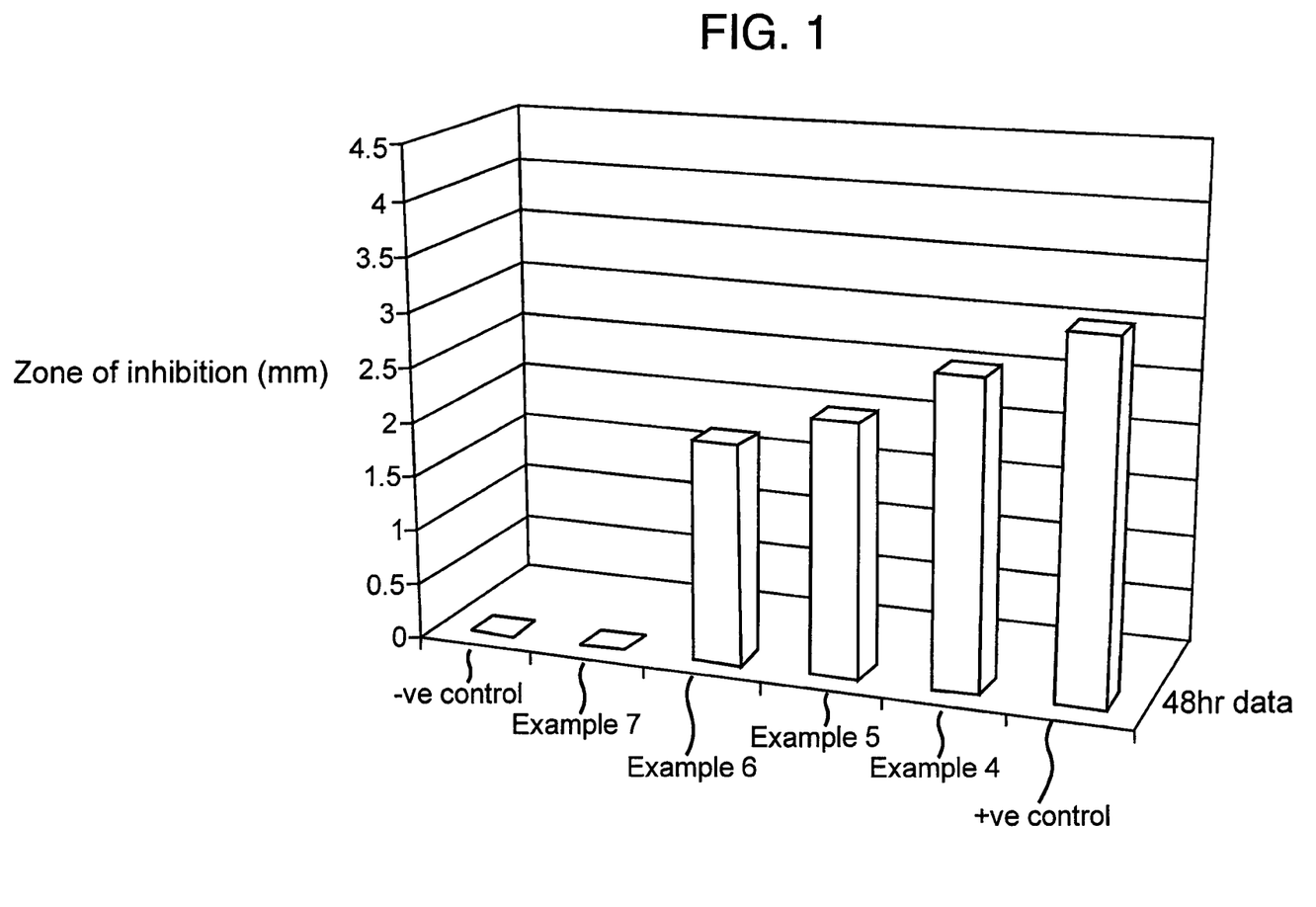
FIG. 1 shows antimicrobial effect against *Staphylococcus Aureus*, plotted as zone of inhibition in mm at 2 days, for a first range of wound dressing material materials.
Figure 2:
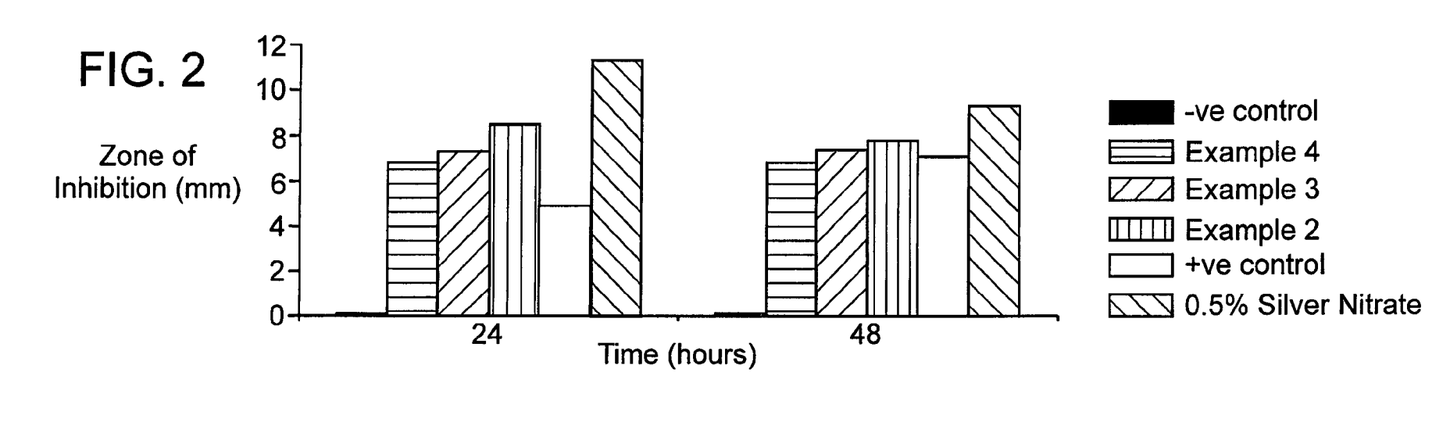
FIG. 2 shows antimicrobial effect against *Staphylococcus Aureus*, plotted as zone of inhibition in mm at 24 and 48 hours, for a second range of wound dressing material materials.

Referring to FIGS. 1 and 2, it can be seen that significant bactericidal effects were observed against *Staphylococcus aureus* for the materials containing 1% silver-ORC and above. The performance was comparable to that of the ACTICOAT dressing.

Figure 3:
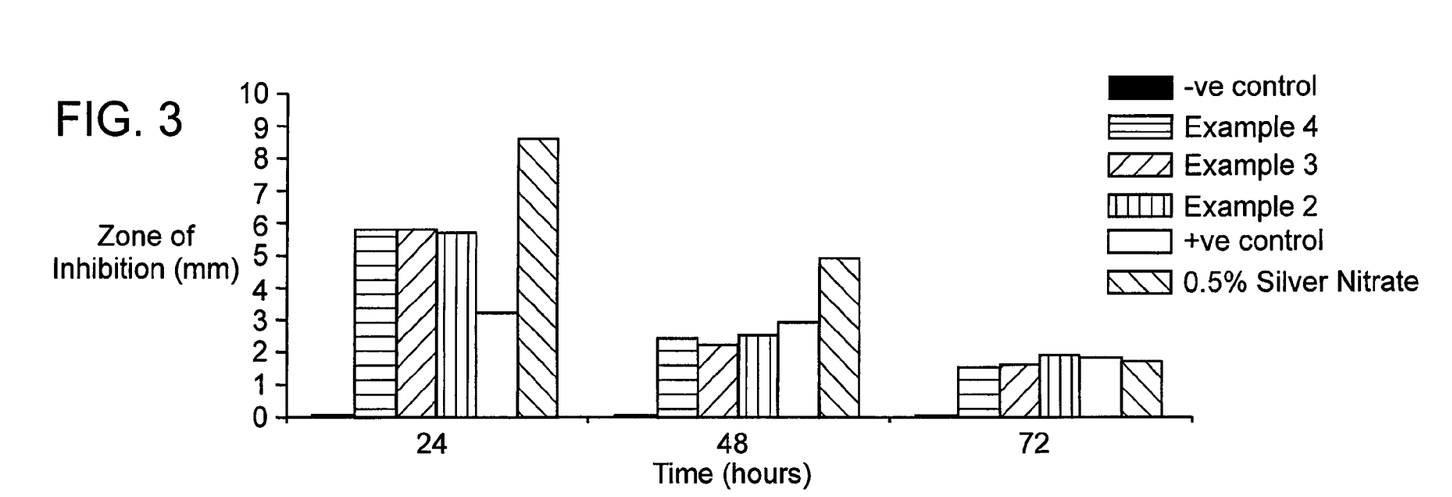
FIG. 3 shows antimicrobial effect against *Pseudomonas Aeruginosa*, plotted as zone of inhibition in mm at 24 and 48 hours, for the second range of wound dressing material materials.

Referring to FIG. 3, it can be seen that significant bactericidal effects were observed against *Pseudomonas Aeruginosa* for the materials containing 10% silver-ORC and above. The performance at 24 hours was superior to that of the ACTI-COAT dressing.

Figure 5:
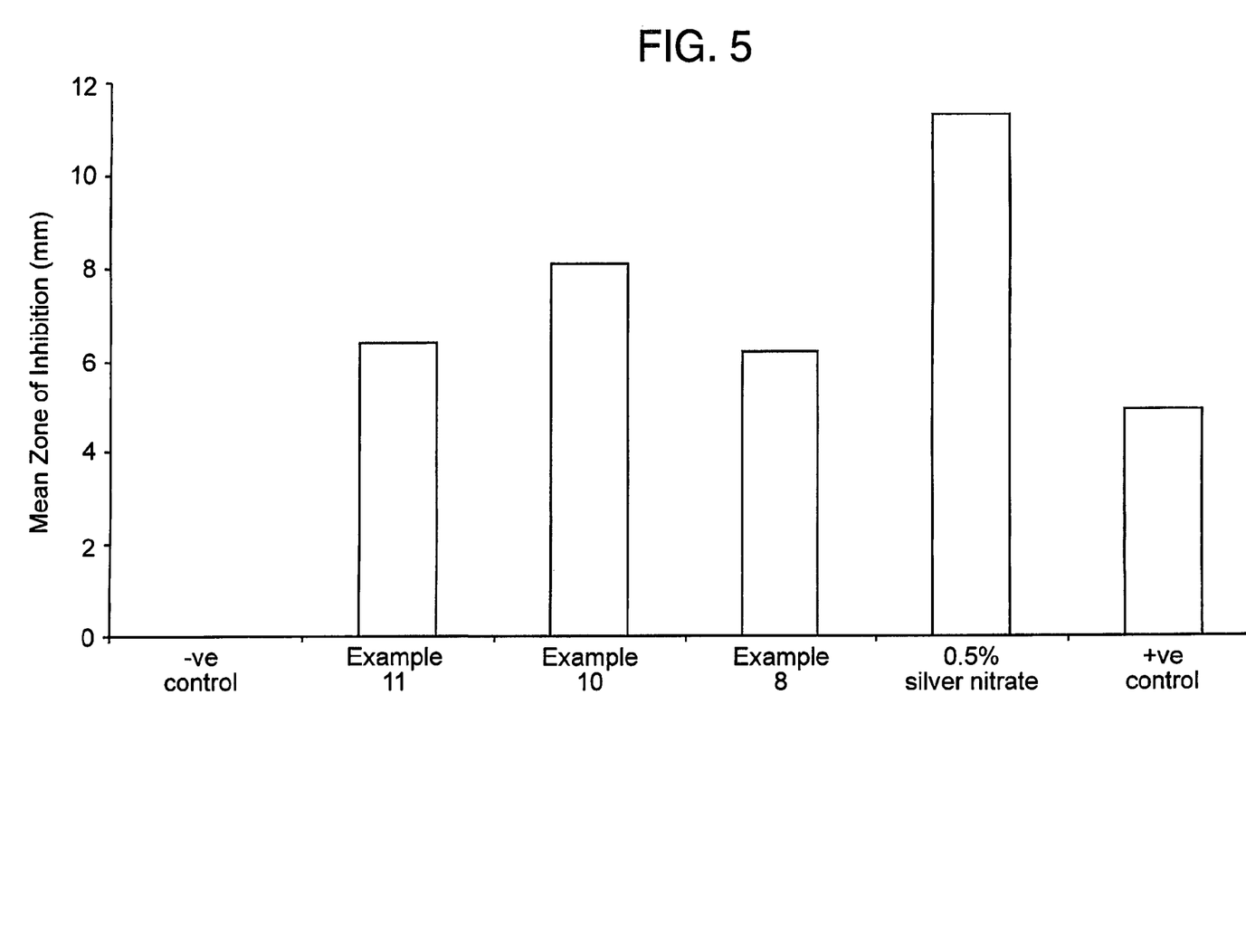
FIG. 5 shows antimicrobial effect against *Staphylococcus Aureus*, plotted as zone of inhibition in mm at 2 days, for a fourth range of wound dressing material materials.

The bactericidal activity of the sponges prepared in Examples 8, 10 and 11 was tested on *Pseudomonas Aeruginosa* by looking at zone of inhibition in the same way as described above. Again, a 55% collagen/45% ORC sponge was used as a negative control, and silver nitrate solution (0.5%) and ACTICOAT were used as positive controls. The results at 48 hours were shown in FIG. 5. It can be seen that the sponges made with collagen-silver complexes show similar zones of inhibition to the positive controls and to the silver-ORC examples of FIG. 3.

Procedure 2

The antiproliferative effects of the dressings from the above Examples were assessed as follows.

Prototype extracts were prepared as follows—1 mg of each wound dressing material to be tested was placed in 1 ml of serum free medium and incubated for 24 hours at 37° C. under sterile conditions.

Adult human dermal fibroblasts were grown and maintained in DMEM 10% FBS (standard culture medium; Dulbecco's miminal essential medium; foetal bovine serum). These cells were routinely subcultured and used for experimental testing when 95% confluent. Adult human dermal fibroblasts were harvested at 95% confluency and re-seeded in a 96-well microtitre plate (100 μl/well) in DMEM+10% FBS at a cell density of $2.5 \times 10^4$ cells/ml. Cells were allowed to adhere to the plate surface for 24 hours in a humidified incubator at 37° C., 5% $CO_2$. The medium was then removed by aspiration and the cell monolayer washed with serum-free DMEM. Test samples (extracts of each prototype) were then added to the cell monolayer (100 μl/well), and 6 replicates of each concentration tested. Serum-containing growth medium (10% FBS in DMEM) was used as a positive control, and serum-free medium was used as a negative control. All samples were incubated with the cells for 48 hours at 37° C., 5% $CO_2$. After this incubation period the conditioned medium was removed by aspiration and replaced with a labelling solution from a commercial cell proliferation kit (XTT, Cell Proliferation kit II, Cat. No. 1 465 015, obtained from Boehringer Mannheim). Once this solution was added an initial absorbance reading was obtained at 450 nm, after which the microtitre plate was incubated at 37° C., 5% $CO_2$ and the absorbance monitored over 4 hours. The proliferative effect of each prototype was evaluated by comparing the absorbance readings measured against the positive and negative controls.

As a positive control, a freeze dried sponge of 45% ORC/55% collagen without any silver was tested, since this was already known to promote fibroblast proliferation.

ACTICOAT was used as a negative control, since it was generally known that the effect of silver on cells in culture was toxic with cell death occurring at high concentrations.

Figure 4:
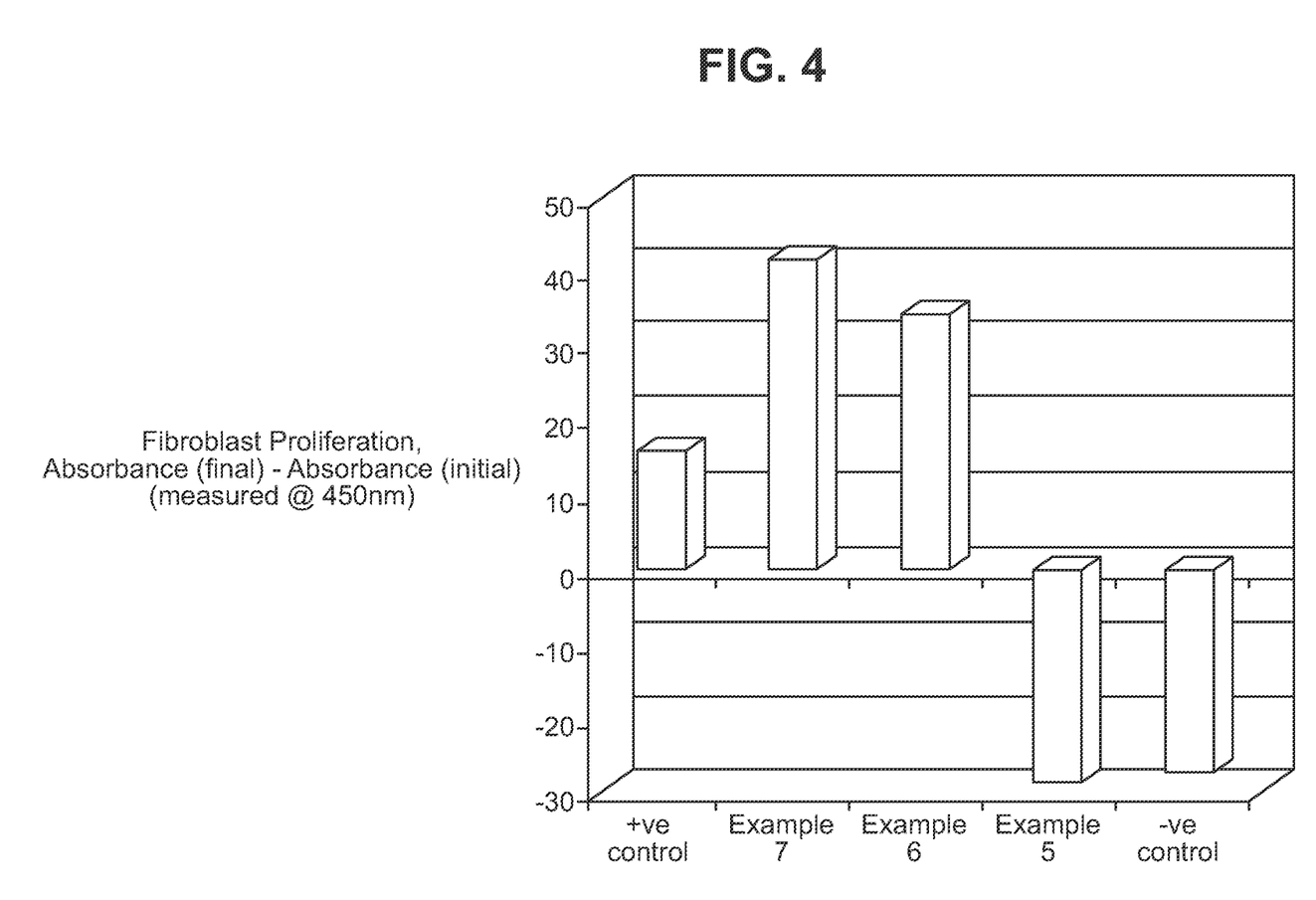
FIG. 4 shows the effect on cell proliferation of extracts from a third range of wound dressing material materials.

The results shown in FIG. 4 were very surprising. It can be seen that the samples containing 0.2% and 1% of the silver-ORC complex strongly promote fibroblast proliferation. This effect was a least double that observed with collagen/ORC, alone which has been shown previously to stimulate cell proliferation. This stimulatory effect was apparently limited to lower concentrations of silver-ORC, as concentrations of 2% and above were detrimental to cell growth. The ACTICOAT control in this experiment shows the expected negative effect on fibroblast proliferation.

Figure 6:
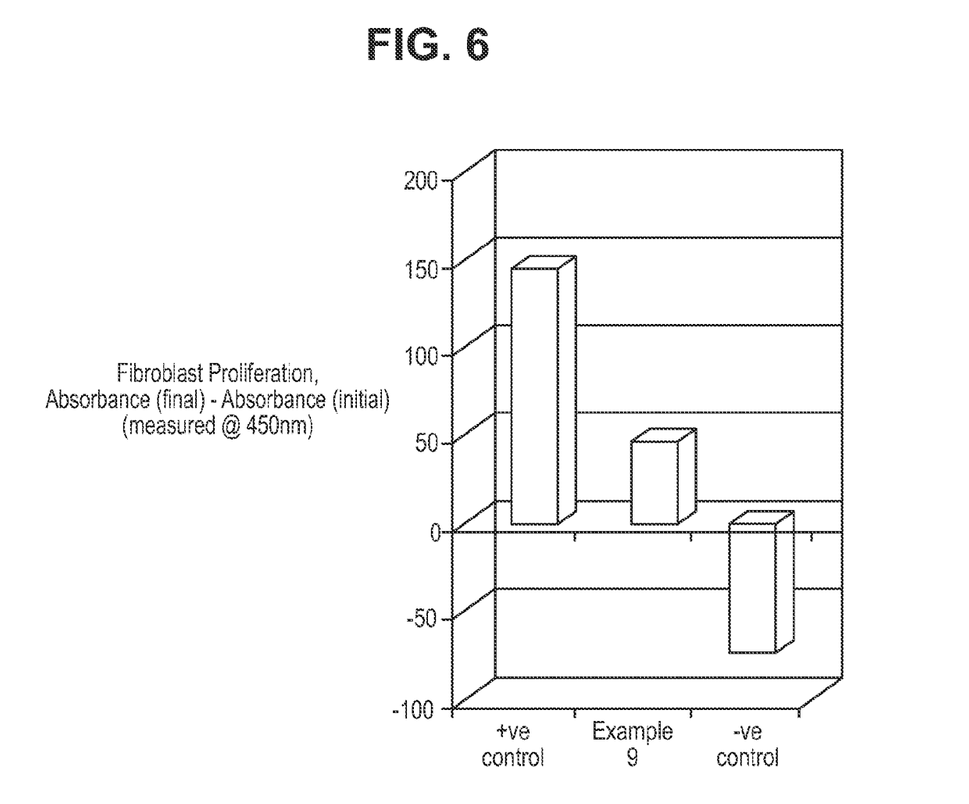
FIG. 6 shows the effect on cell proliferation of extracts from a fifth range of wound dressing material materials.

Referring to FIG. 6, it can be seen that the sample of collagen/ORC material made with 45% silver-collagen, 10% unmodified collagen, and 45% ORC (Example 9) was also stimulatory for fibroblast proliferation, but not as stimulatory as the collagen/ORC positive control.

Procedure 3

The anti-inflammatory potential of the wound dressing materials according to the invention was studied as follows.

Lipopolysaccharide (LPS) has been shown to induce TNF-α and IL-1 production in monocyte macrophage cells. This response can be used to assess anti-inflammatory potential of wound dressings, as TNF-α and IL-1 are known to potentate the inflammation process.

To assess the anti-inflammatory properties of the wound dressing materials, samples were incubated in the presence and absence of lipopolysaccharide (*E. Coli* 055.B5, Sigma Chemical Co.) with monocyte macrophages (THP-1 cells from the European Collection of Cell Cultures). As positive and negative controls, various reference dressing materials and varying concentrations of silver acetate were also incubated with THP-1 cells in the presence and absence of LPS. The concentrations of silver acetate ranged from 0.01 M to 0.001 mM. Silver acetate is known to be cytotoxic at the highest concentrations in this range, and to have no cytotoxicity at the low end. The levels of both TNF-α and IL-1 produced by the THP-1 cells were measured over a 24 hour time period after addition of LPS.

The following wound dressing materials were tested:
(A) A freeze-dried sponge wound dressing material according to the present invention containing 1 wt. % of a silver/ORC complex, prepared as described above in Example 6;
(B) A freeze-dried sponge consisting of 55 wt. % collagen and 45% ORC prepared as described in EP-A-1153622 and available under the Registered Trade Mark PROMOGRAN from Johnson & Johnson Wound Care (Control example); and
(C) A medical gauze available under the Registered Trade Mark SOF-WICK from Johnson & Johnson Wound Care (Control Example).

The experimental procedure was as follows.

The THP-1 cells were maintained in low LPS 10% FBS. Cells were then spun down at 1000 rpm for 10 minutes and re-suspended to give a concentration of 10,000 cells per ml. PMA (Phorbol 12-myristate 13-acetate, Sigma Chemical Co.) was then added to the cell suspension to give a final concentration of $2.4 \times 10^{-7}$ M.

This cell suspension was then used to seed 24 well microtiter plates with 10 000 cells/well. Plates were then incubated at 36° C., 5% $CO_2$ for 72 hours to allow adherence of cells to the tissue culture plastic.

RPMI medium containing 1 mg/ml of LPS was then prepared. (LPS was reconstituted at 1 mg/ml in sterile phosphate buffered saline). After incubation, the PMA medium on the 24 well microtitre plates was removed via aspiration and replaced with RPMI+LPS or RPMI medium alone.

6 mm punch samples from the materials to be tested were removed and soaked in PBS for no more than 2 minutes. Two specimens of each dressing material type were sampled four times to give a total of eight samples for each dressing type. Silver acetate solutions were prepared in RPMI media to give concentration of 0.1 M, 10 mM, 1 mM and 0.1 mM.

The pre-soaked dressing biopsies and different concentrations of silver acetate were then added to the microtiter plate. 10 μl of each silver acetate solution was added to each test wells giving test concentrations of 0.01 M, 1 mM, 0.1 mM and 0.01 mM.

The microtiter plates were then incubated at 37° C., 5% $CO_2$. After 4, 6 and 24 hours incubation 20 μl aliquots of conditioned media were removed from each well. Samples were transferred to bullet tubes and stored at −70° C. until ELISA analysis.

Before ELISA analysis media samples were divided into 10 μl aliquots and diluted 1:2 with calibrator diluent (calibrator diluent used depended on ELISA being performed). This dilution brought samples within the standard curve range. Manufacturer's instructions for the ELISA kits were followed. The ELISA kits were supplied by R&D Systems Limited.

Standard curves for both TNF-α and IL-1β were plotted and the equations generated were used to convert sample absorbencies to equivalent cytokine concentrations. Average concentrations of both TNF-α and IL-1β were calculated for each sample condition at each time point. These results were then used to compare differences between test conditions over time.

At cytotoxic levels (0.01 M) silver acetate induced cell death and therefore no TNF-α was produced. At sub-cytotoxic levels (0.1 mM, and 0.001 mM) the THP-1 cells remained viable (as determined by microscopic examination) and induced a dose response in the amount of TNF-α produced. 0.01 mM silver acetate showed an ability to inhibit the amount of TNF-α produced, whilst the lowest concentrations of silver acetate studied had no effect on the amount of no TNF-α produced after stimulation with LPS.

Figure 7:
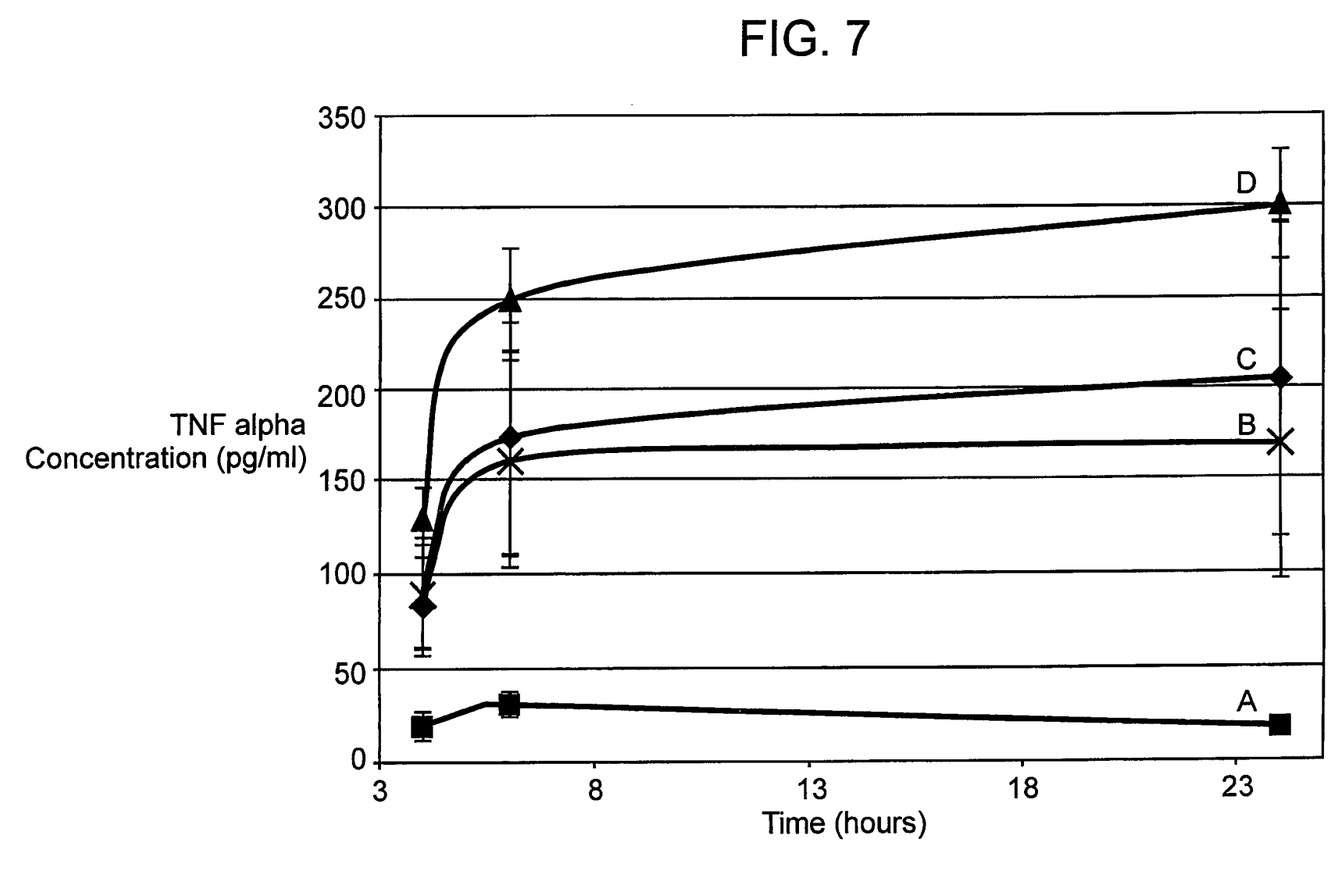
FIG. 7 shows a graph of TNF-a concentration against time for the following wound dressing materials incubated with lipopolysaccharides and monocyte macrophages: (A) a wound dressing material according to the invention, (B) 0.01 M Silver acetate solution, (C) a freeze-dried collagen/ORC dressing without silver, and (D) a conventional wound dressing gauze.

Referring to FIG. 7, it can be seen that the various dressings tested demonstrated different abilities to influence the amount of TNF-alpha produced by THP-1 cells. Gauze (Sample C) had little effect, and cells in the presence of this dressing produced the same level of TNF-α as seen in the positive control (LPS only).

Cells in the presence of a silver-free collagen/ORC sponge dressing (Sample B) produced lower levels of the inflammatory cytokine than seen with LPS alone.

However, when a silver-containing collagen/ORC sponge dressing material according to the present invention (Sample A) was present in the assay well, THP-1 cells produced virtually no TNF-α. The inhibition by the material according to the present invention was, surprisingly, even better that that achieved with silver acetate concentrations (0.01 mM) equivalent to those present in the material.

Results for IL-1β (data not shown) were similar to those shown for TNF-α.

The results indicate an ability of the material according to the present invention to inhibit the production of important inflammatory cytokines by THP-1 monocyte macrophages. This effect was shown to be sustained throughout the 24 hour test period and suggests the material of the present invention has an ability to influence cytokine production over a prolonged time frame. The anti-inflammatory activity of the material according to the present invention could not be predicted from the two components alone.

The Examples have been described for the purpose of illustration only. Many other compositions and methods falling with the scope of the present invention will be apparent to the skilled reader.

The invention claimed is:

1. A wound dressing material comprising a complex of an oxidized regenerated cellulose with silver, wherein the amount of silver in the wound dressing material comprises from about 0.1 wt. % to about 0.3 wt. % silver.

2. A wound dressing material according to claim 1, wherein the amount of silver in the complex is from about 1 to about 50% by weight based on the weight of the oxidized regenerated cellulose.

3. A wound dressing material according to claim 1, in the form of a freeze-dried sponge sheet, or a woven or nonwoven fibrous sheet, or a gel sheet.

4. A wound dressing comprising a wound dressing material according to claim 1.

5. A wound dressing according to claim 4, wherein the wound dressing is sterile and packaged in a microorganism-impermeable container.

6. The wound dressing material of claim 1, wherein the material further comprises collagen.

7. The wound dressing material of claim 6, wherein the material comprises a mixture of collagen and oxidized regenerated cellulose in the weight ratio of 60:40 to 40:60.

8. The wound dressing material of claim 7, wherein the material is a freeze-dried sponge.

9. A method for treating venous ulcers, decubitis ulcers or diabetic ulcers, comprising applying a wound dressing material directly to the surface of the wound; wherein the wound dressing material comprises a complex of oxidized regenerated cellulose with silver, wherein the amount of silver in the wound dressing material comprises from about 0.1 wt. % to about 0.3 wt. % silver.

10. A method of making a wound dressing comprising the steps of:
forming a complex of oxidized regenerated cellulose and silver; and
combining the complex with oxidized regenerated cellulose and collagen;
wherein the wound dressing comprises a cell proliferative amount of silver.

11. The method of claim 10, wherein the wound dressing comprises from about 0.05 wt. % to about 0.3 wt. % silver.

12. The method of claim 11, wherein the wound dressing comprises about 0.25 wt. % silver.

13. The method of claim 10, wherein the wound dressing comprises from about 35 wt. % to about 60 wt. % oxidized regenerated cellulose, from about 60 wt. % to about 35 wt. % collagen and from about 0.5 wt. % to about 5 wt. % of the oxidized regenerated cellulose-silver complex.

14. The method of claim 13, wherein the wound dressing comprises about 44 wt. % of oxidized regenerated cellulose, about 55 wt. % collagen and about 1 wt. % of the regenerated cellulose-silver complex.

15. A wound dressing material comprising a complex of an oxidized regenerated cellulose with silver, wherein the amount of silver in the dressing material comprises a cell proliferative amount of silver in the amount of from about 0.05 wt. % to about 0.3 wt. % silver.

16. The wound dressing material of claim 15, wherein the amount of silver in the wound dressing material is 0.25 wt. % silver.

17. The wound dressing material of claim 16, wherein the wound dressing comprises from about 35 wt. % to about 60 wt. % oxidized regenerated cellulose, from about 60 wt. % to about 35 wt. % collagen and from about 0.5 wt. % to about 5 wt. % of the oxidized regenerated cellulose-silver complex.

18. The wound dressing material of claim 17, wherein the wound dressing comprises about 44 wt. % of the oxidized regenerated cellulose, about 55 wt. % of the collagen and about 1 wt. % of the regenerated cellulose-silver complex.

* * * * *

UNITED STATES PATENT AND TRADEMARK OFFICE
CERTIFICATE OF CORRECTION

PATENT NO. : 8,461,410 B2  Page 1 of 1
APPLICATION NO. : 10/527421
DATED : June 11, 2013
INVENTOR(S) : Cullen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 510 days.

Signed and Sealed this
Eighth Day of September, 2015

Michelle K. Lee
*Director of the United States Patent and Trademark Office*